United States Patent [19]

Porter

[11] 4,253,848

[45] Mar. 3, 1981

[54] METHOD FOR DETERMINING OXIDATIVE STATUS OF UNSATURATED LIPIDS AND METHOD FOR EVALUATING ANTIOXIDANT EFFECTIVENESS IN LIPID-POLYPEPTIDE LAYERS

[75] Inventor: William L. Porter, Cambridge, Mass.

[73] Assignee: The United States of America as represented by the Secretary of the Army, Washington, D.C.

[21] Appl. No.: 114,033

[22] Filed: Jan. 21, 1980

[51] Int. Cl.³ .................. G01N 31/06; G01N 33/02
[52] U.S. Cl. .................. 23/230 HC; 23/230 M; 23/230 PC; 426/231
[58] Field of Search ..... 426/231; 23/230 M, 230 HC, 23/230 PC

[56] References Cited

U.S. PATENT DOCUMENTS

| | | | |
|---|---|---|---|
| 3,689,221 | 9/1972 | Udenfriend | 23/230 M X |
| 3,871,825 | 3/1975 | Leimgburger et al. | 23/230 M |
| 3,892,530 | 7/1975 | Felix et al. | 23/230 M X |
| 4,026,666 | 5/1977 | Holmes | 23/230 M |

OTHER PUBLICATIONS

Gray, J. I., "Measurement of Lipid Oxidation: A Review", J. Amer. Oil Chem. Soc., vol. 55, 1978, pp. 539–546.

*Primary Examiner*—Robert A. Yoncoskie
*Attorney, Agent, or Firm*—Nathan Edelberg; Robert P. Gibson; Lawrence E. Labadini

[57] ABSTRACT

A method for rapid, dry, non-destructive assay of the oxidative status of unsaturated lipids in whole foods, fats or oils and a method for prediction of the storage life of such lipids are disclosed. A method for evaluating the effectiveness of natural or synthetic antioxidants in dry, thin layers of lipid supported on polypeptide is also disclosed. All of these methods depend on the fluorescence of compounds formed by the reaction of volatiles from oxidizing lipids and a polymerized epsilon-caprolactam.

3 Claims, 2 Drawing Figures

METHOD FOR DETERMINING OXIDATIVE STATUS OF UNSATURATED LIPIDS AND METHOD FOR EVALUATING ANTIOXIDANT EFFECTIVENESS IN LIPID-POLYPEPTIDE LAYERS

The invention described herein may be manufactured, used, and licensed by or for the Government for governmental purposes without the payment to me of any royalty thereon.

BACKGROUND OF THE INVENTION

1. Field of the Invention

This invention relates to a non-destructive assay for oxidative status of unsaturated lipids and to a method for evaluation of antioxidant effectiveness in lipid-polypeptide layers.

2. Description of the Prior Art

Lipids can become rancid as a result of oxidation. This rancidity caused by oxidation is a major cause of food deterioration. The acceptability of a food product often depends on the extent to which such deterioration has occurred. Therefore, some technique for assessing the extent of oxidation and for prediction of remaining storage life is necessary. Sensory analysis is one of the most sensitive methods available. However, this method is not practical for routine analysis. As a result, many chemical and physical techniques have been devised in an effort to quantify oxidative deterioration and to correlate the data with off-flavor development. Chemical methods include those which measure peroxide value, the thiobarbituric acid test, the Kreis test, those which measure total and volatile carbonyl compounds, and oxirane determination tests. Physical methods include ultraviolet and infrared spectroscopy, polarography, gas chromatography and refractometry. A more complete review of these various methods for measuring the extent of oxidation can be found in Gray, J. I., J. Amer. Oil Chem. Soc., Vol. 55, pp. 539–546 (1978).

All of the existing chemical methods employ high temperature, or strong acid or solution, which classify them as destructive methods. Prior to the present invention no dry, room temperature, non-destructive objective assay of the storage stability of packaged lipids existed.

SUMMARY OF THE INVENTION

In one aspect, the present invention comprises a method for rapid, dry, room or elevated temperature, non-destructive assay of the oxidation status of unsaturated lipids in packaged, dry, stored whole foods, fats or oils and a method for the prediction of the storage life of such lipids. These methods depend on polyamide fluorescence when in vapor or liquid phase contact with oxidizing lipid. When a polyamide-coated plastic or glass strip is exposed to the oil or in the package atmosphere, dissolved or volatile compounds from oxidizing lipids react with residual contaminant amines in the polyamide layer to form bluish-white-fluorescent compounds which are detectable under ultraviolet light. The fluorescence intensity can be correlated with the oxidative status of the lipid. Successive readings at timed intervals yield a prediction curve for storage life of the lipid. The test can be accelerated by temperature and metals if desired.

In a further aspect, the present invention comprises a method for evaluating the effectiveness of natural or synthetic antioxidants in dry, thin layers of lipid on polypeptide. This method likewise depends on the fluorescence from compounds formed by the reaction of volatiles from oxidizing linoleic acid and a polyamide-coated plastic or glass strip. After a period of time, the fluorescence of a control strip with no antioxidant is compared with the inhibition of fluorescence on a strip with antioxidant. Antioxidant effectiveness may be determined from the ratio of the fluorescence intensity of the control to that of the strip with antioxidant at a given time, or alternatively, from the ratio of times taken to reach a predetermined intensity which corresponds to the end of the typical induction period of other tests. A standard antioxidant at a standard concentration is used for reference.

DESCRIPTION OF THE PREFERRED EMBODIMENT

Figure 1:
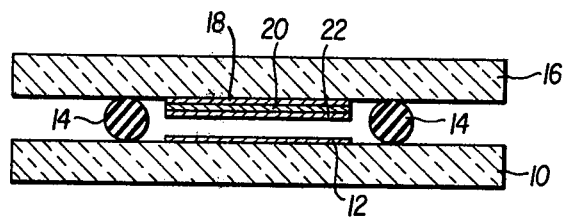
FIG. 1 is a side elevational cross-sectional view of a device suitable for practicing the present invention.

In accordance with the present invention, the extent of oxidation of unsaturated lipids in whole foods, fats or oils can be determined by first exposing a polyamide-coated plastic or glass strip to volatile compounds escaping from an oxidizing lipid. The escaping volatiles react with the polyamide layer to form bluish-white-fluorescent compounds. The mechanism of fluorescent production is the reaction of volatile compounds, consisting primarily of malonaldehyde, with the known residual contaminant amines in the polyamide coating. Because this reaction is analogous to the typical oxidized lipid browning with the free amino groups of proteins and phospholipids in foods, it provides a simultaneous early detection and prediction capability for lipid-amine browning.

The fluorescent compounds which are formed on the polyamide powder are often detectable within about one day by using a hand-held ultraviolet source or in much less time using a solid sample-adapted fluorescence spectrophotometer. The fluorescence intensity for the spot of polyamide exposed to the peroxidizing lipid at an excitation wavelength of 360 nm and emission of 430 nm correlates with the oxidative status of the lipid. Readings can be compared to the very low baseline fluorescence and diffraction spectrum of the unexposed polyamide. Successive readings at regular timed intervals can be plotted to a point of unacceptable lipid oxidation level having the usual sequelae of rancidity, browning and flavor, color and nutrient loss to yield a prediction curve for the storage life of the lipid. The test can be accelerated by temperature and metals. As in all fluorescent determinations, sensitivity is a function of the baseline scatter, diffraction and fluorescence of the unexposed polyamide plate. This fluorescence is much less when the polyamide is coated on glass than when it is coated on the plastic commonly used, polyethylene terephthalate.

The polyamide which is coated onto the glass or plastic strip is a commercially available powdered poly-caprolactam such as PERLON$_{TM}$ or Polyamide-6. The polyamide is a repeating polypeptide of epsilon-aminocaproic acid, with contamination of unpolymerized free primary amino groups. It is essentially neutral in water and has 3.5–4.0% adsorbed surface water as commonly used.

In the practice of the present invention a plate of glass or plastic strip coated with a layer of the polyamide powder is placed in a fluorescence spectrophotometer. The fluorescence index (F.I.), which is the ratio of the intensity at 430 nm to the intensity of the residual, scatter excitation beam at 360 nm, is determined in accordance with the procedures outlined in Kramer R. S. and R. D. Pearlstein, *Science*, 205:693 (1979). The background emission from a fresh polyamide plate has a fluorescence index of 1.5–2.0 arising from a low intensity band pattern caused by diffraction of the excitation beam. The polyamide-coated plate is then exposed to the vapors from a lipid undergoing oxidation. At appropriate intervals, such as every 20 minutes to 1 hour, fluorescence emission spectra of the polyamide-coated plate are recorded. Susceptibility to oxidation, a measure of storage life, is determined by the rate of increase of fluorescence index with time or by the time to reach a given index at a given temperature.

The fluorescence resulting from volatile autoxidation products is visible to the eye if the polyamide-coated plate is viewed from either the uncoated or the coated side using a long wave (360 nm) ultraviolet light. The fluorescence is bluish-white and appears first at the periphery of the coating. This visible fluorescence can be used to avoid repetitious instrumental readings since the fluorescence is detectable by the eye just prior to the onset of rapid autoxidation. This process can be used to determine the oxidative status of lipids in foods such as potato chips and freeze-dried carrots.

A modification of this process permits the testing of microliter quantities of oils. The oil is deposited by capillarity onto the face of a plate coated with polyamide powder. A second polyamide-coated plate is placed so that the polyamide coating faces the oil-treated face of the other plate. The two plates are clamped together separated by a rubber "O" ring. Fluorescence develops on the untreated polyamide plate at room temperature or much more rapidly at elevated temperature. The extent of oxidation can be quantified by fluorescence spectrophotometry or reflection fluorodensitometry, using either intensity at a given time or time to reach a cut-off intensity. Alternatively, the oxidative status of oils can be determined by immersion of a polyamide-coated plate for a suitable time interval at room or elevated temperature, followed by removal from the oil, draining, and instrumental reading of the strip fluorescence intensity. These methods can be used to determine the extent of oxidation of any lipid oil, such as linoleic acid, methyl linoleate, and stripped corn oil.

Thus, in this aspect, the present invention is a method for rapid, dry, room temperature detection of incipient autoxidation in dry foods, fats and oils without any "wet" chemistry or gas chromatography. The method can be quantified and with suitable modifications be made non-destructive using inspection through a window in the package. Field application by a rough visual assay is possible and state of the art modifications by those skilled in the art will permit precise field quantification.

In another aspect, the present invention is a method for evaluating the effectiveness of natural or synthetic antioxidants in dry, thin layers of lipid on polypeptide by measuring the fluorescence of products formed by the reaction of contaminant amines in a polyamide and escaping volatiles from an oxidizing lipid on polypeptide. The methods described above for determining the extent of oxidation of lipids can be modified so that antioxidant effectiveness is measured. In accordance with this aspect of the present invention, a strip or plate of glass or plastic is first coated with a polyamide such as those discussed above. A small amount of the antioxidant to be tested is then deposited onto the polyamide coating. After the antioxidant is dried, linoleic acid is deposited onto the antioxidant. A second plate coated only with polyamide is then exposed to the first plate as the lipid autoxidizes. Another polyamide-coated plate is exposed to a plate coated with polyamide and linoleic acid, but without antioxidant, for comparison. After a period of time, the extent of fluorescence on the polyamide-coated plate exposed to lipid oxidation without antioxidant is compared to the inhibition of fluorescence on the polyamide-coated plate exposed to oxidation in the presence of antioxidant. Comparison can be made either by visual observance of the fluorescence using a long wave ultraviolet lamp or can be quantified using a fluorescence spectrophotometer or a reflection fluorodensitometer with excitation at 360 nm and emission at 430 nm.

Antioxidant effectiveness is determined from the ratio of the fluorescence intensity of the plate exposed to lipid oxidation in the absence of antioxidant to that of the plate exposed to oxidation in the presence of the antioxidant at a given time. Alternatively, antioxidant effectiveness can be determined by the ratio of times taken to reach a predetermined intensity which corresponds to the end of the typical induction period of other tests. A standard antioxidant at a standard concentration is used as a reference.

This method has the advantages of the extreme sensitivity of fluorescence measurement together with rapid dry preparation and testing. The test conditions model the dry, anchored, pauci-layered lipid-protein environment of membranes in dehydrated or intermediate moisture foods, the oxidation of whose polar lipids causes the early rancidity and rejection of whole tissue dry foods. Although the test can be carried out in a few hours at about 65° C., it can be carried out in two days to a week at room temperature. It can also be accelerated by metals, e.g. cobalt, to model that stress.

Thus, this evaluation method provides a rapid, dry, relatively low temperature technique which utilizes the high sensitivity of fluorescence measurement for evaluation of micro amounts of antioxidant. Color of reagents or suspected antioxidant compounds does not interfers, since the detection or evaluation is on the untreated sheet. In addition, evaluation is in a dry, lipid and polypeptide environment similar to that of the susceptible membranes of dehydrated or intermediate moisture foods.

EXAMPLE 1

The following procedure can be used to test the storage or frying life of an autoxidizable oil. A square plate of glass 3 cm×3 cm. is coated with a 120 micron thick layer of polyamide powder (No. G1600/LS 254, Schleicher and Schuell, Keene, N.H., a polymerized epsilon-caprolactam). The coating is scraped to leave a 12 mm. diameter disc of powder on the plate. The plate is placed in a solid sample holder (Model 018-9603, Hitachi-Perkin-Elmer) which is then mounted in a fluorescence spectrophotometer (Model MPF-2A, Hitachi-Perkin-Elmer) with the polyamide coating facing the excitation beam. The fluorescence emission spectra of the plate is recorded at an appropriate sensitivity setting, commencing at 340 nm and ending at 460 nm, using the following settings: excitation at 360 nm, excitation slit width at 2 nm, emission slit width at 4 nm, and filter 39. The intensities at 430 nm and 360 nm are recorded, the latter being the residual scatter peak of the excitation wavelength that penetrates the 39 filter. The following ratio is set up:

$$\frac{\text{Intensity at 430 nm}}{\text{Intensity at 360 nm}} = \text{Fluorescence Index (F.I.)}$$

This ratio is used in all measurements with the 360 nm scatter peak constituting an internal reference. The background emission from a fresh polyamide-coated plate has a fluorescence index of 1.5–2.0 which arises from a low intensity band pattern caused by diffraction of the excitation beam.

A second polyamide-coated glass plate identical to the first is dipped for 1 minute into a 0.25–2.5 mg/ml solution of cobaltous chloride ($CoCl_2.6H_2O$) in distilled water. After draining, the plate is dried in a draft oven at 65° C. Cobalt ion concentration may be varied to attain the desired accelerated rate of autoxidation. Five microliters or about 4.5 mg of the autoxidizable oil to be tested are deposited from a calibrated disposable pipette in the center of the polyamide disc. The oil spreads over the entire disc surface.

Figure 2:
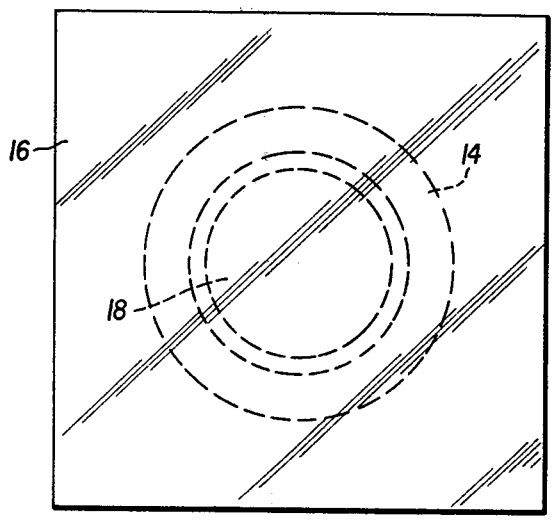
FIG. 2 is a plan view of the device shown in FIG. 1.

The two plates are then assembled as shown in FIGS. 1 and 2. The first glass plate 10 with the polyamide disc 12 is positioned with coated side facing up. A BUNA$_{TM}$ "O" ring (16 mm diameter × 1.7 mm thickness) 14 is then placed on the surface of the plate centered over the polyamide disc. The second plate 16 which is coated with polyamide 18 treated with cobalt 20 and oil 22 is then placed treated side down on top of the "O" ring so that the disc is centered and faces the disc of the bottom plate. This glass sandwich assembly is clamped together by two steel side-opening screw compression pinch corks (not shown).

The sandwich assembly is then placed with the oil-treated plate above the untreated plate on another glass plate on a wire shelf at the center of a 65° C. draft oven. At regular intervals, such as every 20 minutes to 1 hour, the sandwich is disassembled and fluorescence emission spectra of the untreated bottom plate are recorded. Fluorescence indices are computed as described above. The sandwich is then reassembled and placed back in the oven. Susceptibility to oxidation, which is a measure of storage life or frying life is determined by the rate of increase of F.I. with time or by the time to reach a given F.I. at the oven temperature. A high rate or a short elapsed time to critical F.I. indicates high susceptibility to oxidation, and hence, a short storage or frying life. If a series of progressively abused oils are being tested, a control sample of fresh oil is run as above to serve as a reference.

The fluorescence resulting from volatile autoxidation products is visible to the eye if the bottom plate of the sandwich is viewed from either above or below under a long wave (360 nm) ultraviolet light. The fluorescence which is bluish-white appears first as a thin peripheral ring. This visible fluorescent ring can be used to avoid repetitious instrumental readings since the fluorescence is detectable by the eye at the periphery of the disc just prior to the onset of rapid autoxidation. The values given in Table I below illustrate the increase in F.I. in a 60 minute period:

TABLE I

| | F.I. (Initial) | F.I. (60 Minutes) |
|---|---|---|
| Stripped Corn Oil Abused (Oxidized) | 3.1 | 4.0 |
| Linoleic Acid | 3.6 | 14.5 |
| Fresh Linoleic Acid | 2.4 | 5.5 |

EXAMPLE 2

Since fluorescence due to autoxidative products develops at room temperature, albeit more slowly than at elevated temperature, the following technique can be used to monitor the cumulative abuse level of a stored or abused frying oil. Two square glass plates are prepared with discs of polyamide powder as described in Example 1. If it is desired to continuously monitor the abuse level of the oil, one of the plates is immersed in the fresh oil in its container prior to sealing. Alternatively, the plate may simply be exposed to the atmoshpere above the oil in the closed container. At regular intervals, the fluorescence is observed through the glass or certain plastic containers using a hand-held long-wave UV lamp or by fluorescence emission spectrophotometry as described in Example 1. The cumulative fluorescence is computed in a manner similar to that for storage life above. The fluorescence index of the abused oil is then compared to that of the fresh plate previously determined. As in Example 1, fluorescence detectable by the eye usually just precedes instrumental change and can be used as a warning monitor.

EXAMPLE 3

Since the autoxidative products which produce fluorescence are volatile at ambient conditions, the techniques described in Example 1 and 2 can be modified to monitor the cumulative abuse level of a stored dry whole tissue food. A polyamide-coated glass plate prepared as described in Example 1 is exposed within the closed package and after an appropriate storage interval the fluorescence emission spectra and F.I. are measured. Visual monitoring can be made through the glass and some plastic food containers. This method is susceptible to non-destructive quantitative monitoring using contact fluorescence spectrophotometry in modified equipment. In this Example pulverized potato chips and freeze-dried carrots were placed in separate petri dishes so as to occupy almost two-thirds of the volume of the dish. Polyamide coated glass plates were suspended by means of tape over the containers of each dish, powder side down and spaced from the contents. The glass cover of the petri dish is added to complete the package. A control was prepared in similar fashion containing only the polyamide glass plate within the covered petri dish. All four dishes were held in an oven at 65° C. for 72 hours and the F.I. for each is as follows:

| Control | 4.6 |
|---|---|
| Carrots | 6.9 |
| Potato Chips | 9.5 |

EXAMPLE 4

The following procedure can be employed to measure the effectiveness of an antioxidant. A square 3 cm × 3 cm plate of terephthalate-plastic coated with 100 micron thickness of polyamide powder (Polygram or Polyamide-6, a polymerized epsilon-caprolactam with ultraviolet indicator, Macherey-Nagel and Co.) is scraped to leave a 12 mm disc of powder at the center of the plate. The plate is mounted in a fluorescence spectrophotometer, fluorescence emission spectra are recorded, and fluorescence index (F.I.) determined according to the procedures described in Example 1 above.

Onto the disc of a second polyamide-coated plate identical to the first, 10 ul of an absolute ethanol solution containing 0.1 mg/ml of the antioxidant to be tested is deposited by adsorption from a disposable micropipette. The plate is dried under a stream of dry nitrogen. Five microliters or about 4.5 mg of linoleic acid are deposited onto the discs of both the antioxidant-treated plate and the untreated plate from a disposable micropipette. The oil soon spreads on both discs to cover the entire disc surfaces. Alternatively, the antioxidant may be incorporated into the test substrate, linoleic acid, at a concentration of 0.02 weight percent by rotary evaporator removal of solvent from an ethanolic solution of the antioxidant and the linoleic acid, e.g., 1 ml linoleic acid plus 1 ml ethanol containing 0.2 mg of antioxidant. Two additional polyamide-coated plates are scraped to leave a 12 mm disc of polyamide powder on each. These plates are not treated with either linoleic acid or with antioxidant and linoleic acid.

The four plates are then assembled in a manner similar to that shown in FIGS. 1 and 2 discussed in Example 1. One of the untreated plates is positioned with the polyamide disc facing upward. A BUNA$_{TM}$ "O" (16 mm diameter × 1.7 mm thickness) is placed on the surface of the plate centered over the polyamide disc. The first plate treated with antioxidant and linoleic acid is then placed treated side down on top of the "O" ring so that the disc is centered over the ring and facing the disc on the other plate. The sandwich is then clamped with two steel side-opening screw compression pinch cocks. A second sandwich assembly is prepared in the same manner as the first using the other untreated polyamide-coated plate as the bottom plate and the second polyamide-coated plate treated only with linoleic acid is placed on top of the "O" ring facing down.

The two sandwich assemblies are then placed on a glass plate on a wire shelf at the center of a draft oven at 65° C. with their untreated plates resting on the glass plate. At regular intervals, such as every hour, the sandwiches are disassembled and fluorescence emission spectra of both bottom plates are recorded. Fluorescence indices are computed as described in Example 1. The sandwiches are then reassembled and placed back in the oven.

The relative effectiveness of an antioxidant is determined using the following procedure. The bottom plates facing both control and antioxidant-treated linoleic acid will show an induction period of low, relatively constant fluorescence index (F.I.) followed by a rapid increase in value. This increase in F.I. will be delayed when antioxidant is present. On a plot of F.I. versus time, two tangents can be drawn along the curve at the area of rapid increase and at the area of relatively constant F.I. The time corresponding to the intersection of the two tangents is the induction period in each case. The relative effectivenss of the antioxidant is then computed as follows:

$$\text{Relative effectiveness} = \frac{\text{Induction period with antioxidant}}{\text{Induction period without antioxidant}}$$

The bluish-white fluorescence resulting from volatile autoxidation products is visible to the eye if the bottom plate of the sandwich is viewed from the powder face direction under a long wave (360 nm) ultraviolet light. This visible fluorescence can be used to avoid repetitious instrumental readings since the fluorescence is detectable by the eye just prior to the onset of rapid autoxidation.

What is claimed is:

1. A method for determining the existing oxidation level of unsaturated lipids in whole foods, fats or oils, comprising:
   (a) coating a substrate with a polymerized epsilon-caprolactam comprising a repeating polypeptide of epsilon-amino caproic acid with contamination of unpolymerized free primary amino groups;
   (b) measuring the residual excitation beam scattering and the diffraction and fluorescence emission spectrum of the coated substrate and computing its fluorescence index (F.I.);
   (c) exposing the coated substrate to volatile compounds escaping from an oxidizing lipid;
   (d) measuring the residual excitation beam scattering and the diffraction and fluorescence emission spectrum of the compounds on the coated substrate formed by reaction of the volatile compounds and the contaminant amines in the coating and computing their fluorescence index (F.I.); and
   (e) ascertaining the existing oxidation level by determining the difference between the F.I. computed in step (b) and the F.I. computed in step (d).

2. A method for determining the storage or frying life of unsaturated lipids in whole foods, fats or oils, comprising:
   (a) coating two substrates with a polymerized epsilon-caprolactam comprising a repeating polypeptide of epsilon-amino caproic acid with contamination of unpolymerized free primary amino groups;
   (b) exposing the first coated substrate to volatile compounds escaping from an oxidizing lipid of known oxidative status for a period of time starting when the lipid is fresh and ending when the lipid is rancid;
   (c) measuring the residual excitation beam scattering and the diffraction and fluorescence emission spectrum of the compounds on the first coated substrate formed by reaction of the volatile compounds and the contaminant amines in the coating and computing their fluorescence index (F.I.) at regular intervals of time;
   (d) exposing the second coated substrate to volatile compounds escaping from an oxidizing lipid of the same type used in step (b) but having an unknown oxidative status;
   (e) measuring the residual excitation beam scattering and the diffraction and fluorescence emission spectrum of the compounds on the second coated substrate formed by reaction of the volatile compounds and the contaminant amines in the coating and computing their fluorescence index (F.I.); and
   (f) comparing the F.I. computed in step (e) with the second F.I. computed in step (c) to ascertain the storage or frying life of the lipid.

3. A method for determining the relative effectiveness of an antioxidant in a lipid-polypeptide layer, comprising:
  (a) coating two substrates with a polymerized epsilon-caprolactam comprising a repeating polypeptide of epsilon-amino caproic acid with contamination of unpolymerized free primary amino groups;
  (b) exposing the first coated substrate to volatile compounds escaping from an oxidizing lipid for a period of time starting when the lipid is fresh and ending when the lipid is rancid;
  (c) measuring the residual excitation beam scattering and the diffraction and fluorescence emission spectrum of the compounds on the first coated substrate formed by reaction of the volatile compounds and the contaminant amines in the coating and computing their fluorescence index (F.I.) at regular intervals of time;
  (d) exposing the second coated substrate to volatile compounds escaping from an oxidizing lipid in the presence of the antioxidant being tested for a period of time starting when the lipid is fresh and ending when the lipid is rancid;
  (e) measuring the residual excitation beam scattering and the diffraction and fluorescence emission spectrum of the compounds on the second coated substrate formed by reaction of the volatile compounds and the contaminant amines in the coating and computing their fluorescence index (F.I.) at regular intervals of time;
  (f) plotting the fluorescence indices computed in step (c) versus time and determining the induction period without antioxidant present;
  (g) plotting the fluorescence indices computed in step (e) versus time and determining the induction period with antioxidant present; and
  (h) determining the relative effectiveness of the antioxidant being tested by dividing the induction period with antioxidant present by the induction period without antioxidant present.

* * * * *